United States Patent
Ingmanson et al.

(10) Patent No.: US 10,236,616 B2
(45) Date of Patent: Mar. 19, 2019

(54) ADAPTER ASSEMBLY FOR INTERCONNECTING SURGICAL DEVICES AND SURGICAL ATTACHMENTS, AND SURGICAL SYSTEMS THEREOF

(71) Applicant: Covidien LP, Mansfield, MA (US)

(72) Inventors: Michael Ingmanson, Stratford, CT (US); Matthew Chowaniec, Middletown, CT (US); Ramiro Cabrera, Cheshire, CT (US)

(73) Assignee: Covidien LP, Mansfield, MA (US)

( * ) Notice: Subject to any disclaimer, the term of this patent is extended or adjusted under 35 U.S.C. 154(b) by 996 days.

(21) Appl. No.: 14/513,283

(22) Filed: Oct. 14, 2014

(65) Prior Publication Data

US 2015/0150547 A1   Jun. 4, 2015

Related U.S. Application Data

(60) Provisional application No. 61/911,774, filed on Dec. 4, 2013.

(51) Int. Cl.
 *A61B 17/00* (2006.01)
 *H01R 13/46* (2006.01)
 *A61B 17/072* (2006.01)

(52) U.S. Cl.
 CPC ....... *H01R 13/46* (2013.01); *A61B 17/07207* (2013.01); *A61B 2017/0046* (2013.01); *A61B 2017/00367* (2013.01); *A61B 2017/00389* (2013.01); *A61B 2017/00398* (2013.01); *A61B 2017/00464* (2013.01); *A61B 2017/00477* (2013.01); *A61B 2017/00734* (2013.01); *Y10T 29/49117* (2015.01)

(58) Field of Classification Search
 CPC .......... A61B 17/00; A61B 2017/00477; H01R 13/46
 USPC ............................................. 606/1
 See application file for complete search history.

(56) References Cited

U.S. PATENT DOCUMENTS

| | | |
|---|---|---|
| 2,777,340 A | 1/1957 | Hettwer et al. |
| 2,957,353 A | 10/1960 | Babacz |
| 3,111,328 A | 11/1963 | Di Rito et al. |
| 3,695,058 A | 10/1972 | Keith, Jr. |
| 3,734,515 A | 5/1973 | Dudek |

(Continued)

FOREIGN PATENT DOCUMENTS

| | | |
|---|---|---|
| AU | 2008229795 A1 | 4/2009 |
| CA | 2451558 A1 | 1/2003 |

(Continued)

OTHER PUBLICATIONS

Extended European Search Report corresponding to International Application No. EP 15 15 1076.5 dated Apr. 22, 2015.

(Continued)

*Primary Examiner* — John R Downey

(57) ABSTRACT

An adapter assembly selectively interconnects a surgical device with a surgical attachment that is configured to perform at least one function. The adapter assembly includes a proximal end that includes at least one mating part adapted to be detachably connected to a surgical device and configured to permit coupling of the adapter assembly to a surgical device in at least a first connection orientation and a second connection orientation.

7 Claims, 5 Drawing Sheets

(56) References Cited

U.S. PATENT DOCUMENTS

| | | | |
|---|---|---|---|
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,632,432 A | 5/1997 | Schulze et al. |
| 5,647,526 A | 7/1997 | Green et al. |
| 5,653,374 A | 8/1997 | Young et al. |
| 5,658,300 A | 8/1997 | Bito et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,797,536 A | 8/1998 | Smith et al. |
| 5,820,009 A | 10/1998 | Melling et al. |
| 5,863,159 A | 1/1999 | Lasko |
| 5,865,361 A | 2/1999 | Milliman et al. |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,869,320 B2 * | 3/2005 | Haas ............... H01R 13/514 439/701 |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |

(56) References Cited

U.S. PATENT DOCUMENTS

| | | |
|---|---|---|
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 * | 6/2011 | Whitman ......... A61B 17/07207 227/175.1 |
| 7,967,178 B2 | 6/2011 | Scirica et al. |
| 7,967,179 B2 | 6/2011 | Olson et al. |
| 7,992,758 B2 | 8/2011 | Whitman et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,056,787 B2 | 11/2011 | Boudreaux et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,303,581 B2 | 11/2012 | Arts et al. |
| 8,342,379 B2 | 1/2013 | Whitman et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,752,749 B2 | 6/2014 | Moore et al. |
| 8,758,391 B2 | 6/2014 | Swayze et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0111012 A1 | 6/2004 | Whitman |
| 2004/0133189 A1 | 7/2004 | Sakurai |
| 2004/0176751 A1 | 9/2004 | Weitzner et al. |
| 2004/0193146 A1 | 9/2004 | Lee et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola et al. |
| 2007/0023476 A1 | 2/2007 | Whitman et al. |
| 2007/0023477 A1 * | 2/2007 | Whitman ......... A61B 17/07207 227/175.1 |
| 2007/0029363 A1 | 2/2007 | Popov |
| 2007/0055219 A1 | 3/2007 | Whitman et al. |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |

(56) References Cited

U.S. PATENT DOCUMENTS

| | | | |
|---|---|---|---|
| 2009/0209990 A1* | 8/2009 | Yates | A61B 17/07207 606/169 |
| 2009/0254094 A1 | 10/2009 | Knapp et al. | |
| 2009/0314821 A1 | 12/2009 | Racenet | |
| 2010/0069942 A1 | 3/2010 | Shelton, IV | |
| 2010/0193568 A1 | 8/2010 | Scheib et al. | |
| 2010/0211053 A1 | 8/2010 | Ross et al. | |
| 2010/0225073 A1 | 9/2010 | Porter et al. | |
| 2011/0006101 A1 | 1/2011 | Hall et al. | |
| 2011/0017801 A1 | 1/2011 | Zemlok et al. | |
| 2011/0071508 A1 | 3/2011 | Duval et al. | |
| 2011/0077673 A1 | 3/2011 | Grubac et al. | |
| 2011/0121049 A1 | 5/2011 | Malinouskas et al. | |
| 2011/0125138 A1 | 5/2011 | Malinouskas et al. | |
| 2011/0139851 A1 | 6/2011 | McCuen | |
| 2011/0155783 A1 | 6/2011 | Rajappa et al. | |
| 2011/0155786 A1 | 6/2011 | Shelton, IV | |
| 2011/0172648 A1 | 7/2011 | Jeong | |
| 2011/0174099 A1* | 7/2011 | Ross | A61B 17/072 74/89.32 |
| 2011/0204119 A1 | 8/2011 | McCuen | |
| 2011/0218522 A1 | 9/2011 | Whitman | |
| 2011/0253765 A1* | 10/2011 | Nicholas | A61B 17/07207 227/175.1 |
| 2011/0276057 A1 | 11/2011 | Conlon et al. | |
| 2011/0290854 A1 | 12/2011 | Timm et al. | |
| 2011/0295242 A1 | 12/2011 | Spivey et al. | |
| 2011/0295269 A1 | 12/2011 | Swensgard et al. | |
| 2012/0000962 A1 | 1/2012 | Racenet et al. | |
| 2012/0074199 A1 | 3/2012 | Olson et al. | |
| 2012/0089131 A1* | 4/2012 | Zemlok | A61B 17/07207 606/1 |
| 2012/0104071 A1 | 5/2012 | Bryant | |
| 2012/0116368 A1 | 5/2012 | Viola | |
| 2012/0143002 A1 | 6/2012 | Aranyi et al. | |
| 2012/0172924 A1 | 7/2012 | Allen, IV | |
| 2012/0223121 A1 | 9/2012 | Viola et al. | |
| 2012/0245428 A1 | 9/2012 | Smith et al. | |
| 2012/0253329 A1 | 10/2012 | Zemlok et al. | |
| 2012/0310220 A1 | 12/2012 | Malkowski et al. | |
| 2012/0323226 A1 | 12/2012 | Chowaniec et al. | |
| 2012/0330285 A1* | 12/2012 | Hartoumbekis | A61B 17/0218 606/1 |
| 2013/0018361 A1 | 1/2013 | Bryant | |
| 2013/0093149 A1 | 4/2013 | Saur et al. | |
| 2013/0098966 A1 | 4/2013 | Kostrzewski et al. | |
| 2013/0098968 A1 | 4/2013 | Aranyi et al. | |
| 2013/0098969 A1 | 4/2013 | Scirica et al. | |
| 2013/0181035 A1 | 7/2013 | Milliman | |
| 2013/0184704 A1 | 7/2013 | Beardsley et al. | |
| 2013/0214025 A1 | 8/2013 | Zemlok et al. | |
| 2013/0240596 A1 | 9/2013 | Whitman | |
| 2013/0274722 A1 | 10/2013 | Kostrzewski et al. | |
| 2013/0282052 A1 | 10/2013 | Aranyi et al. | |
| 2013/0292451 A1 | 11/2013 | Viola et al. | |
| 2013/0313304 A1 | 11/2013 | Shelton, IV et al. | |
| 2013/0317486 A1 | 11/2013 | Nicholas et al. | |
| 2013/0319706 A1 | 12/2013 | Nicholas et al. | |
| 2013/0324978 A1 | 12/2013 | Nicholas et al. | |
| 2013/0324979 A1 | 12/2013 | Nicholas et al. | |
| 2013/0334281 A1 | 12/2013 | Williams | |
| 2014/0012236 A1 | 1/2014 | Williams et al. | |
| 2014/0012237 A1 | 1/2014 | Pribanic et al. | |
| 2014/0012289 A1 | 1/2014 | Snow et al. | |
| 2014/0025046 A1 | 1/2014 | Williams et al. | |
| 2014/0110455 A1 | 4/2014 | Ingmanson et al. | |
| 2014/0144970 A1 | 5/2014 | Aranyi et al. | |
| 2014/0207125 A1 | 7/2014 | Applegate et al. | |
| 2014/0207182 A1 | 7/2014 | Zergiebel et al. | |
| 2014/0207185 A1 | 7/2014 | Goble et al. | |
| 2014/0236173 A1 | 8/2014 | Scirica et al. | |
| 2014/0236174 A1 | 8/2014 | Williams et al. | |
| 2014/0276932 A1 | 9/2014 | Williams et al. | |
| 2014/0299647 A1 | 10/2014 | Scirica et al. | |
| 2014/0303668 A1 | 10/2014 | Nicholas et al. | |
| 2014/0358129 A1 | 12/2014 | Zergiebel et al. | |
| 2014/0361068 A1 | 12/2014 | Aranyi et al. | |
| 2014/0373652 A1 | 12/2014 | Zergiebel et al. | |
| 2015/0048144 A1 | 2/2015 | Whitman | |
| 2015/0076205 A1 | 3/2015 | Zergiebel | |
| 2015/0080912 A1 | 3/2015 | Sapre | |
| 2015/0157321 A1 | 6/2015 | Zergiebel et al. | |
| 2015/0164502 A1 | 6/2015 | Richard et al. | |
| 2015/0272577 A1 | 10/2015 | Zemlok et al. | |
| 2015/0297199 A1 | 10/2015 | Nicholas et al. | |
| 2015/0303996 A1 | 10/2015 | Calderoni | |
| 2015/0320420 A1 | 11/2015 | Penna et al. | |
| 2015/0327850 A1 | 11/2015 | Kostrzewski | |
| 2015/0342601 A1 | 12/2015 | Williams et al. | |
| 2015/0342603 A1 | 12/2015 | Zergiebel et al. | |
| 2015/0374366 A1 | 12/2015 | Zergiebel et al. | |
| 2015/0374370 A1 | 12/2015 | Zergiebel et al. | |
| 2015/0374371 A1 | 12/2015 | Richard et al. | |
| 2015/0374372 A1 | 12/2015 | Zergiebel et al. | |
| 2015/0374449 A1 | 12/2015 | Chowaniec et al. | |
| 2015/0380187 A1 | 12/2015 | Zergiebel et al. | |
| 2016/0095585 A1 | 4/2016 | Zergiebel et al. | |
| 2016/0095596 A1 | 4/2016 | Scirica et al. | |
| 2016/0106406 A1 | 4/2016 | Cabrera et al. | |
| 2016/0113648 A1 | 4/2016 | Zergiebel et al. | |
| 2016/0113649 A1 | 4/2016 | Zergiebel et al. | |

FOREIGN PATENT DOCUMENTS

| | | |
|---|---|---|
| CN | 101856251 A | 10/2010 |
| CN | 102068289 A | 5/2011 |
| CN | 102247182 A | 11/2011 |
| DE | 102008053842 A1 | 5/2010 |
| EP | 0634144 A1 | 1/1995 |
| EP | 0648476 A1 | 4/1995 |
| EP | 0686374 A2 | 12/1995 |
| EP | 0705571 A1 | 4/1996 |
| EP | 1690502 A1 | 8/2006 |
| EP | 1723913 A1 | 11/2006 |
| EP | 1736112 A1 | 12/2006 |
| EP | 1759652 A2 | 3/2007 |
| EP | 1769754 A1 | 4/2007 |
| EP | 1772105 A1 | 4/2007 |
| EP | 1 813 203 A2 | 8/2007 |
| EP | 1813199 A1 | 8/2007 |
| EP | 1813211 A2 | 8/2007 |
| EP | 1908412 A2 | 4/2008 |
| EP | 1917929 A1 | 5/2008 |
| EP | 1943954 A2 | 7/2008 |
| EP | 1943956 A2 | 7/2008 |
| EP | 1943958 A1 | 7/2008 |
| EP | 1943976 A2 | 7/2008 |
| EP | 1952769 A2 | 8/2008 |
| EP | 2005898 A2 | 12/2008 |
| EP | 2027819 A1 | 2/2009 |
| EP | 2044890 A1 | 4/2009 |
| EP | 2055243 A2 | 5/2009 |
| EP | 2090247 A1 | 8/2009 |
| EP | 2098170 A2 | 9/2009 |
| EP | 2100561 A2 | 9/2009 |
| EP | 2100562 A2 | 9/2009 |
| EP | 2165664 A2 | 3/2010 |
| EP | 2236098 A2 | 10/2010 |
| EP | 2245994 A1 | 11/2010 |
| EP | 2263568 A2 | 12/2010 |
| EP | 2272443 A1 | 1/2011 |
| EP | 2316345 A1 | 5/2011 |
| EP | 2324776 A2 | 5/2011 |
| EP | 2329773 A1 | 6/2011 |
| EP | 2333509 A1 | 6/2011 |
| EP | 2377472 A1 | 10/2011 |
| EP | 2462878 A1 | 6/2012 |
| EP | 2462880 A2 | 6/2012 |
| EP | 2491872 A1 | 8/2012 |
| EP | 2586382 A2 | 5/2013 |
| EP | 2606834 A2 | 6/2013 |
| EP | 2668910 A2 | 12/2013 |
| EP | 2676615 A2 | 12/2013 |

(56) References Cited

FOREIGN PATENT DOCUMENTS

| | | | |
|---|---|---|---|
| EP | 2815705 A1 | 12/2014 |
| ES | 2333509 A1 | 2/2010 |
| FR | 2861574 A1 | 5/2005 |
| JP | 08-038488 | 2/1996 |
| JP | 2005-125075 A | 5/2005 |
| KR | 20120022521 A | 3/2012 |
| WO | 99/15086 A1 | 4/1999 |
| WO | 2000/072760 A1 | 12/2000 |
| WO | 2000/072765 A1 | 12/2000 |
| WO | 2003/000138 A2 | 1/2003 |
| WO | 2003/026511 A1 | 4/2003 |
| WO | 2003/030743 A2 | 4/2003 |
| WO | 2003065916 A1 | 8/2003 |
| WO | 2003/077769 A1 | 9/2003 |
| WO | 2003090630 A2 | 11/2003 |
| WO | 2004/107989 A1 | 12/2004 |
| WO | 2006/042210 A2 | 4/2006 |
| WO | 2007016290 A2 | 2/2007 |
| WO | 2007/026354 A1 | 3/2007 |
| WO | 2007137304 A2 | 11/2007 |
| WO | 2008/131362 A2 | 10/2008 |
| WO | 2008/133956 A2 | 11/2008 |
| WO | 2009039506 A1 | 3/2009 |
| WO | 2007014355 A3 | 4/2009 |
| WO | 2009/132359 A2 | 10/2009 |
| WO | 2009/143092 A1 | 11/2009 |
| WO | 2009149234 A1 | 12/2009 |
| WO | 2011/108840 A2 | 9/2011 |
| WO | 2012040984 A1 | 4/2012 |

OTHER PUBLICATIONS

Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
European Search Report dated Sep. 20, 2017, corresponding to European Application No. 17176329.5; 10 pages.
European Search Report, dated Apr. 13, 2015, corresponding to European Patent Application No. 14196027.8; 9 pages.
Chinese Office Action (with English translation), dated Feb. 7, 2018, corresponding to Chinese Application No. 2014107349051; 22 total pages.

* cited by examiner

ADAPTER ASSEMBLY FOR INTERCONNECTING SURGICAL DEVICES AND SURGICAL ATTACHMENTS, AND SURGICAL SYSTEMS THEREOF

CROSS-REFERENCE TO RELATED APPLICATIONS

This application claims the benefit of and priority to U.S. Provisional Patent Application No. 61/911,774, filed Dec. 4, 2013, the entire disclosure of which is incorporated by reference herein

BACKGROUND

1. Technical Field

The present disclosure relates to adapter assemblies for use in surgical systems. More specifically, the present disclosure relates to adapter assemblies for use with electromechanical surgical devices to electrically and mechanically interconnect electromechanical surgical devices and surgical attachments, such as, for example, surgical loading units. Surgical systems including hand held electromechanical surgical devices and adapter assemblies for connecting surgical loading units to a hand held electromechanical surgical device are also described.

2. Background of Related Art

A number of surgical device manufacturers have developed product lines with proprietary drive systems for operating and/or manipulating electromechanical surgical devices. In many instances the electromechanical surgical devices include a handle assembly, which is reusable, and disposable loading units and/or single use loading units. The loading units are selectively connected to the handle assembly prior to use and then disconnected from the handle assembly following use in order to be disposed of or in some instances sterilized for re-use.

In certain instances, an adapter assembly is used to interconnect an electromechanical surgical device with any one of a number of surgical attachments, such as, for example, surgical loading units, to establish a mechanical and/or electrical connection therebetween. Presently, however, electromechanical surgical devices are limited to being connected with adapter assemblies in only one connection orientation, which limits a versatility and a comfort of use of the surgical device. For example, if a practitioner reverses an orientation of a surgical device relative to his or her hand, the actuators used to actuate the functions of the surgical attachment will also be reversed relative to the practitioner's hand, making operation of the surgical device unfamiliar to the practitioner.

Further, surgical devices often include several motors used to drive the function of different parts of a surgical attachment. Each part requires a unique amount of torque, speed and/or runtime, which leads to an inconsistent lifespan for each motor. Also, if a particular motor were to fail, a specific function of the surgical attachment driven by that motor would become non-operational.

Accordingly, a need exists for an adapter assembly that can connect to a surgical device and/or a surgical attachment in more than one connection orientation so that an electromechanical surgical system can be provided that overcomes at least the above-mentioned deficiencies of the prior art.

SUMMARY

In one aspect, the present disclosure relates to adapter assemblies for use with electromechanical surgical devices to electrically and mechanically interconnect electromechanical surgical devices and surgical attachments. In another aspect, the present disclosure relates to surgical systems including hand held electromechanical surgical devices and adapter assemblies for connecting surgical attachments to the hand held electromechanical surgical devices.

According to an aspect of the present disclosure, adapter assemblies for selectively interconnecting a surgical device with a surgical attachment are provided. In embodiments, the adapter assembly has a proximal end that includes at least one mating part adapted to be detachably connected to a surgical device. The at least one mating part may be configured to permit coupling of the adapter assembly to the surgical device in at least a first connection orientation and a second connection orientation.

In embodiments, the at least one mating part includes a plurality of mating parts aligned in a symmetrical configuration. In embodiments, the adapter assembly is configured to determine a connection orientation with the surgical device. The adapter assembly may be configured to interchange functions actuated by the surgical device when the connection orientation moves between the first connection orientation and the second connection orientation.

In embodiments, the adapter assembly is configured to reverse functions actuated by at least two actuators of the surgical device when the connection orientation rotates between the first connection orientation and the second connection orientation.

In embodiments, the at least one mating part includes an electrical connector adapted to be connected to an electrical connector of the surgical device such that the electrical connector of the at least one mating part determines the connection orientation between the adapter assembly and the surgical device.

According to another aspect of the present disclosure, an electromechanical surgical system is provided. In embodiments, the electromechanical surgical system comprises a hand-held electromechanical surgical device configured to actuate a surgical attachment. The surgical device may include a housing and at least one motor disposed with the housing for driving movement of the surgical attachment. An adapter assembly may selectively interconnect the surgical device with the surgical attachment. In embodiments, the adapter assembly is in operative communication with the at least one motor. The adapter assembly may include at least one mating part adapted to be detachably connected with at least one of the surgical device and the surgical attachment. In embodiments, the at least one mating part is configured to permit coupling of the adapter assembly to the surgical device in at least a first connection orientation and a second connection orientation.

In embodiments, the surgical device includes a first actuator and a second actuator. The actuators may be configured to actuate a different function of the surgical attachment. In embodiments, in the first connection orientation the first actuator actuates a first function of the surgical attachment and the second actuator actuates a second function of the surgical attachment. In the second connection orientation the first actuator may actuate the second function and the second actuator may actuate the first function. In embodiments, the first and second actuators include user input buttons.

In embodiments, the at least one motor may include a first motor adapted to be connected to a first drive shaft of the adapter assembly for performing a first function of the surgical attachment. The at least one motor may further include a second motor adapted to be connected to a second drive shaft of the adapter assembly for performing a second function of the surgical attachment. In embodiments, in the first connection orientation the first motor is coupled with the first drive shaft and the second motor is coupled with the second drive shaft. In the second connection orientation the first motor is coupled with the second drive shaft and the second motor is coupled with the first drive shaft.

In embodiments, the adapter assembly and the surgical device are connectable in a plurality of orientations. Each orientation of the plurality of orientations can correspond to a different rate of motion of the surgical attachment when the surgical attachment is actuated.

In embodiments, the adapter assembly is configured to interchange functions actuated by the surgical device when the connection orientation moves between the first connection orientation and the second connection orientation. In embodiments, the adapter assembly is configured to reverse functions actuated by at least two actuators of the surgical device when the connection orientation rotates between the first connection orientation and the second connection orientation.

In embodiments, the adapter assembly is configured to determine a connection with the surgical device. The at least one mating part may include an electrical connector adapter for connection to an electrical connector of the surgical device such that the electrical connector of the adapter assembly can determine the connection orientation with the surgical device.

According to a further aspect of the present disclosure, a method of assembling an electromechanical surgical system is provided. In embodiments, the method comprises providing a surgical attachment. A hand-held electromechanical surgical device may also be provided, which is configured to actuate the surgical attachment. In embodiments, the surgical device includes a housing including a first actuator and a second actuator, and at least one motor disposed with the housing for driving movement of the surgical attachment. In embodiments, an adapter assembly is provided. The adapter assembly may include at least one mating part configured to permit coupling of the adapter assembly to the surgical device in one of a first connection orientation and a second connection orientation. The surgical device can be connected with the surgical attachment via the adapter assembly in a selected one of the first and second connection orientations.

In embodiments, the method of assembling an electromechanical surgical system further includes reversing functions actuated by the actuators when the adapter assembly is connected to the surgical device in another of the first connection orientation and the second connection orientation.

In embodiments, the surgical device and the surgical attachment are adapted to be connected via the adapter assembly in a plurality of connection orientations. Each connection orientation of the plurality of connection orientations may correspond to a different rate of motion of the surgical attachment such that the rate of motion of the surgical attachment is adjustable via adjustment of the connection orientations.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1A:
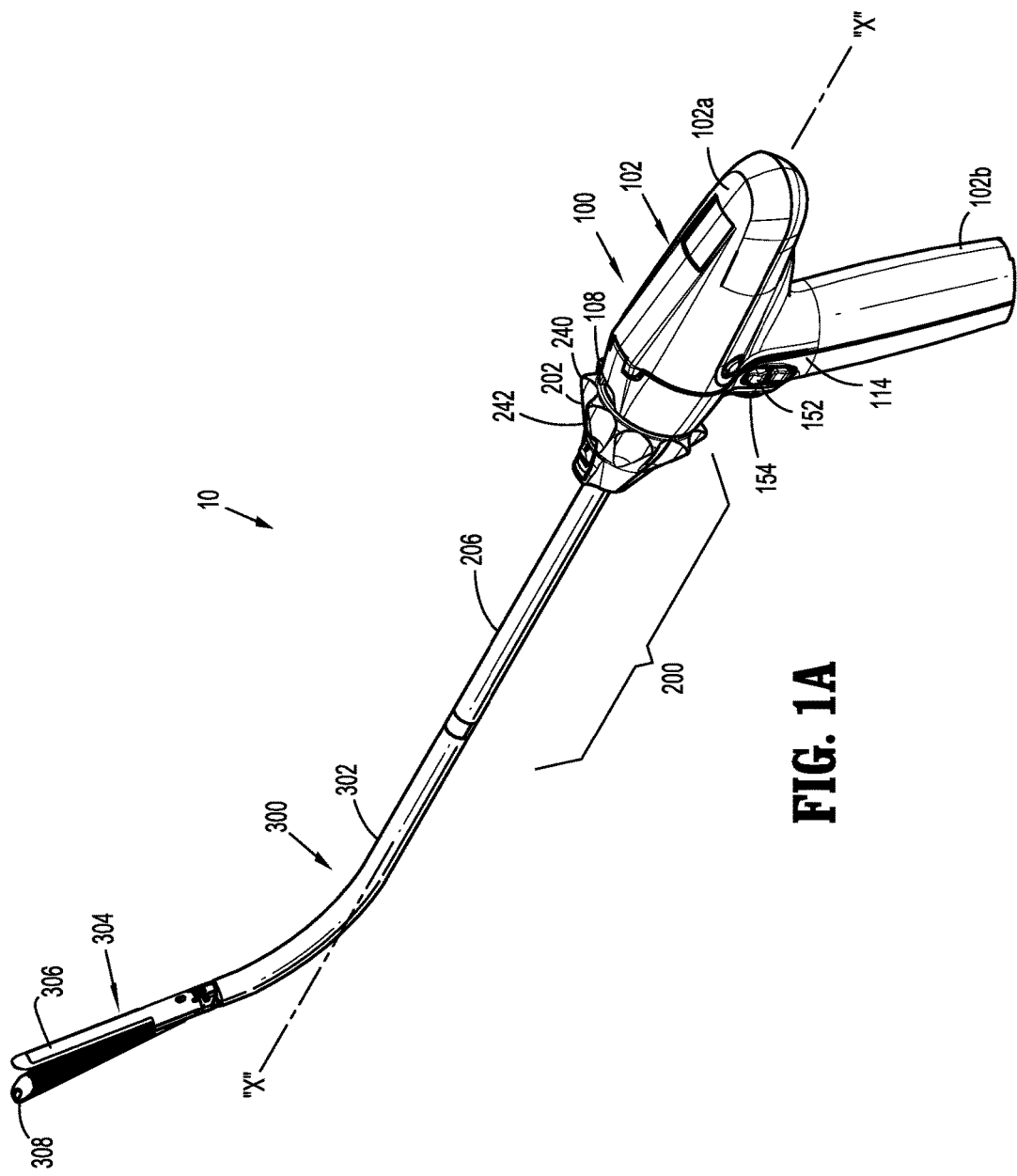
FIG. 1A is a perspective view of an electromechanical surgical system, with an adapter assembly connected with a surgical device in a first connection orientation, in accordance with an embodiment of the present disclosure.

Embodiments of the presently disclosed surgical devices, adapter assemblies, and surgical attachments are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

A surgical device, in accordance with an embodiment of the present disclosure, is generally designated as 100, and is in the form of a powered hand held electromechanical surgical device configured for selective attachment thereto of a plurality of different end effectors. The end effectors may be any one of various surgical attachments including, but not limited to a surgical stapler, a surgical cutter, a surgical stapler-cutter, a linear surgical stapler, a linear surgical stapler-cutter, a circular surgical stapler, a circular surgical stapler-cutter, a surgical clip applier, a surgical clip ligator, a surgical clamping device, a vessel expanding device, a lumen expanding device, a scalpel, a fluid delivery device or any other type of surgical instrument. Each of the surgical attachments is configured for actuation and manipulation by the powered hand held electromechanical surgical device.

Figure 1B:
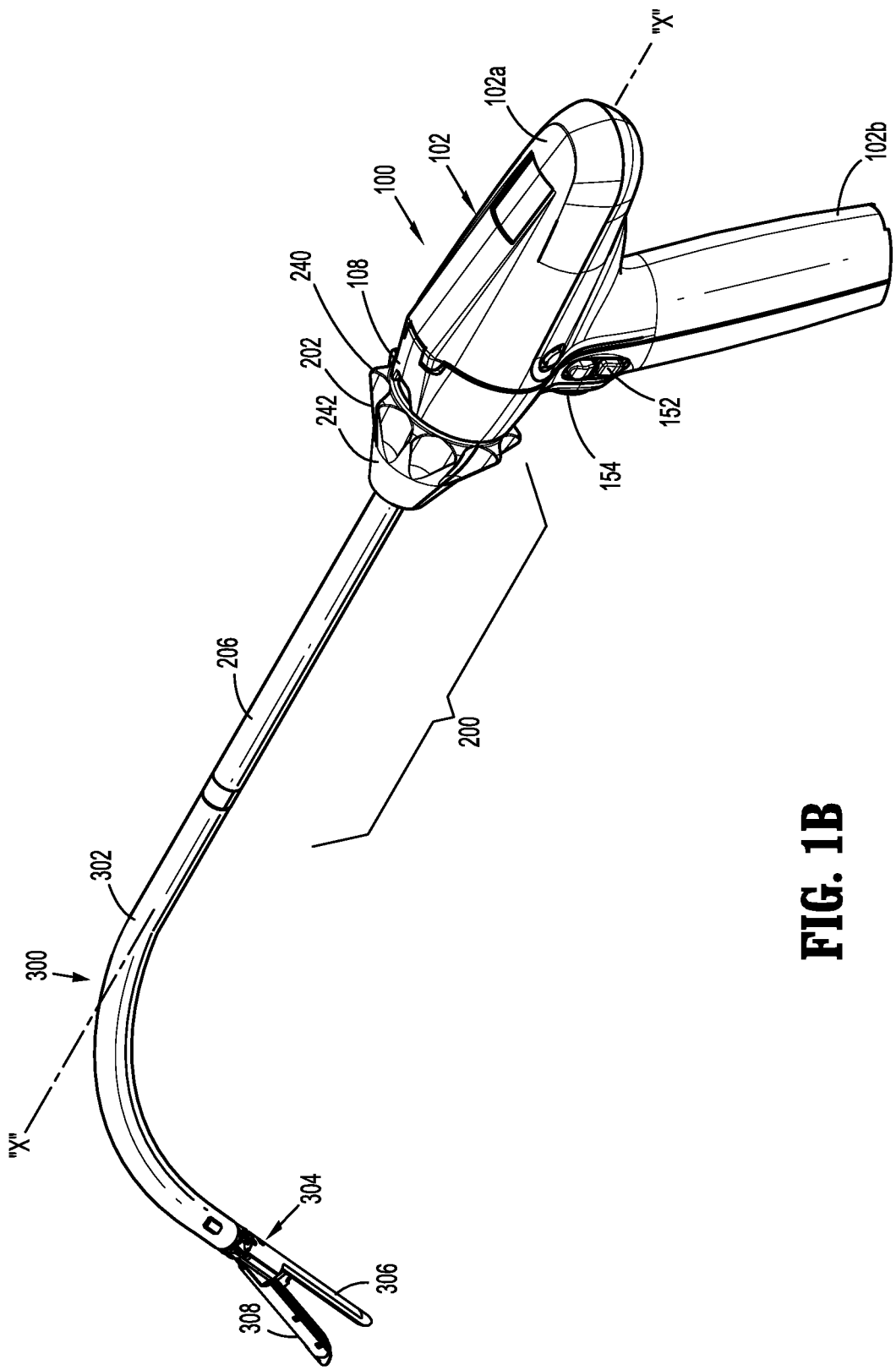
FIG. 1B is a perspective view of the system shown in FIG. 1A, with the adapter assembly connected with the surgical device in a second connection orientation.

As illustrated in FIGS. 1A and 1B, a surgical system is provided, such as, for example, an electromechanical surgical system 10. System 10 includes hand-held electromechanical surgical device 100 configured for selective connection with an adapter assembly 200, and, in turn, adapter assembly 200 is configured for selective connection with a surgical attachment 300 (e.g., an end effector, multiple- or single-use loading unit, see FIG. 4) that is configured to perform at least one function. Surgical device 100 is configured and adapted to actuate surgical attachment 300. Adapter assembly 200 is connectable with surgical device 100 in at least a first connection orientation, as shown, for example, in FIG. 1A, and a second connection orientation, as shown, for example, in FIG. 1B, as described herein.

As illustrated in FIGS. 1A and 1B, surgical device 100 includes a housing, such as, for example, a handle housing 102 including a circuit board (not shown) and a drive mechanism (not shown) situated therein. The circuit board is configured to control the various operations of surgical device 100. Handle housing 102 defines a cavity therein (not shown) for selective removable receipt of a rechargeable battery (not shown) therein. The battery is configured to supply power to any of the electrical components of surgical device 100 including electric motors used to drive the operation of surgical attachment 300.

Handle housing 102 includes an upper housing portion 102a which houses various components of surgical device 100, and a lower hand grip portion 102b extending from upper housing portion 102a. Lower hand grip portion 102b may be disposed distally of a proximal-most end of upper housing portion 102a. In some embodiments, lower hand grip portion 102b has various surface features, such as, for example, knurled, smooth, rough, and/or textured to enhance a practitioner's gripping of lower hand grip portion 102b.

Handle housing 102 provides a housing in which a drive mechanism is situated. The drive mechanism is configured to drive shafts and/or gear components in order to perform the various operations of surgical device 100. In particular, the drive mechanism is configured to drive shafts and/or gear components in order to selectively move a tool assembly 304 of surgical attachment 300 (see FIG. 4) relative to a proximal body portion 302 of surgical attachment 300, to rotate surgical attachment 300 about a longitudinal axis relative to handle housing 102, to move/approximate an anvil assembly 306 and a cartridge assembly 308 of surgical attachment 300 relative to one another, and/or to fire a stapling and cutting cartridge within cartridge assembly 308 of surgical attachment 300.

Figure 2:
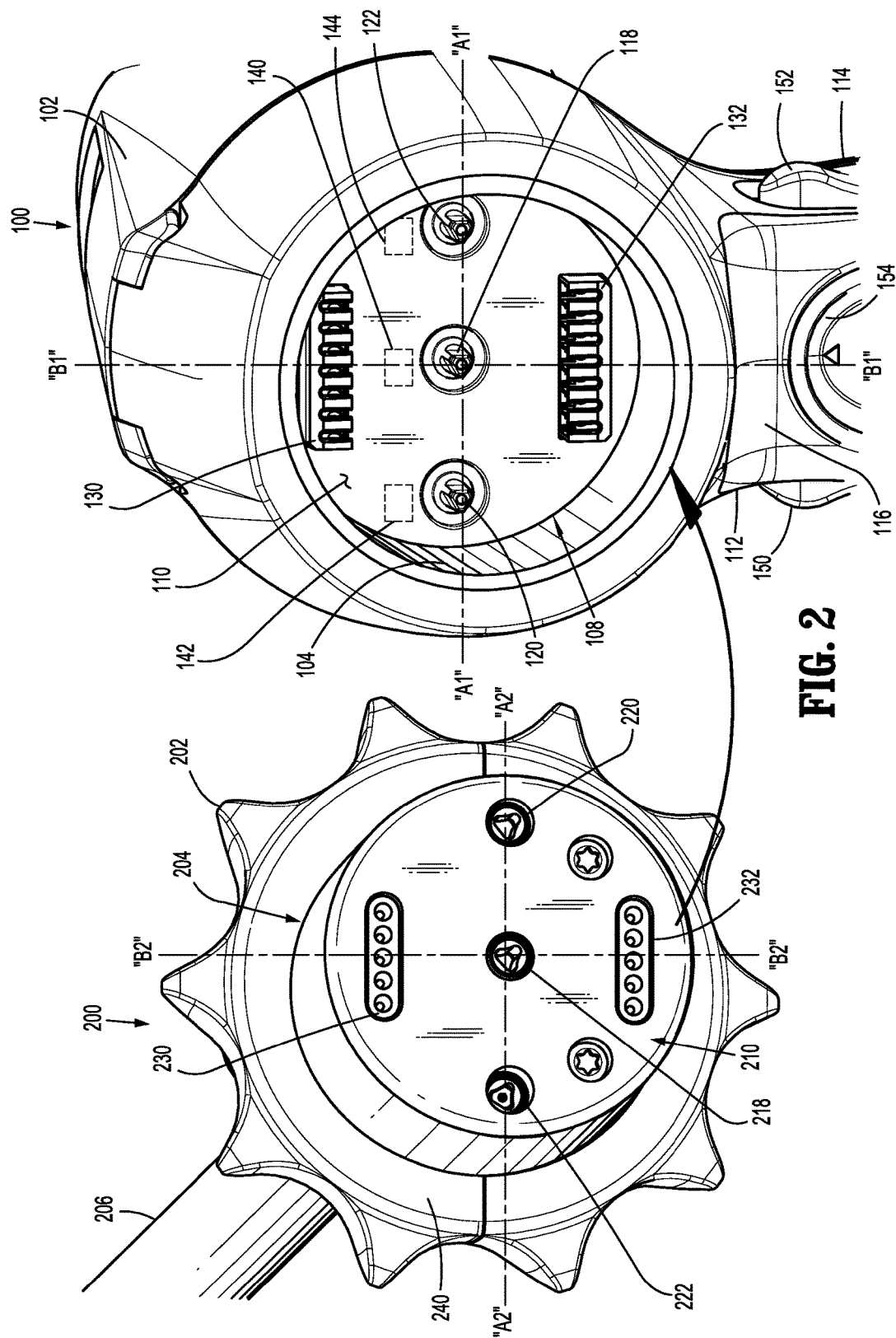
FIG. 2 is a front, perspective view of an adapter assembly and a surgical device of the system shown in FIGS. 1A and 1B in a disconnected configuration.

As illustrated in FIG. 2, handle housing 102 includes a recess 104 formed in a surface thereof that defines a female mating part, such as, for example, a connection portion 108 configured to accept a correspondingly shaped male mating part 210 of adapter assembly 200 in various orientations, such as, for example, a first connection orientation and a second connection orientation. Connection portion 108 includes a planar face 110 and a substantially circular configuration. In some embodiments, connection portion 108 has alternative configurations, such as, for example, oval, oblong, triangular, square, rectangular, hexagonal, polygonal, or star-shaped, configured for mating engagement with correspondingly shaped male mating part 210 of adapter assembly 110.

Connection portion 108 houses three rotatable drive connectors 118, 120, 122 protruding from planar face 110. Rotatable drive connectors 118, 120, 122 are arranged in a common plane or line "A1-A1" with one another such that rotatable drive connectors 118, 120, 122 are aligned in a symmetrical configuration. Additionally, in the embodiment illustrated in FIGS. 2 and 3, it is contemplated that a second and a third drive connector 120, 122 may be spaced an equal distance from a first drive connector 118.

In one embodiment, rotatable drive connectors 118, 120, 122 may be arranged in a circular pattern. It is contemplated that rotatable drive connectors 118, 120, 122 may be arranged in various configurations, such as, for example, those alternatives described herein above or below. In some embodiments, connection portion 108 may house more than three rotatable drive connectors.

Planar face 110 of connection portion 108 further includes a first electrical connector, such as, for example, a first electrical plug/receptacle 130 and a second electrical connector, such as, for example, a second electrical plug/receptacle 132, each being disposed on opposite sides of the plane "A1-A1" intersecting rotatable drive shafts 118, 120, 122. Electrical plugs/receptacles 130, 132 are configured for electrical connection with either a first set of electrical contact pins 230 or a second set of electrical contact pins 232 of adapter assembly 200 depending on an orientation of adapter assembly 200 relative to surgical device 100. Contact pin sets 230, 232 may be supported on a circuit board (not shown), as will be described in greater detail herein below. Electrical plugs 130, 132 may be symmetrically spaced about first drive connector 118 along a plane "B1-B1." It is contemplated that connection portion 108 may include more than two electrical plugs. In some embodiments, connection portion 108 may include a plurality of electrical plugs/receptacles circumferentially disposed about rotatable drive connectors 118, 120, 122.

Surgical device 100 includes a first motor 140, a second motor 142 and a third motor 144 (e.g., electric motors), shown in phantom in FIG. 2. Motors 140, 142, 144 are disposed within handle housing 102 for driving movement of surgical attachment 300 via adapter assembly 200 that is connected to rotatable drive connectors 118, 120, 122. Motors 140, 142, 144 are connected to rotatable drive connectors 118, 120, 122, respectively, so that each motor 140, 142, 144 separately drives the rotation of each rotatable drive connector 118, 120, 122.

As illustrated in FIGS. 1A, 1B and 2, handle housing 102 supports a plurality of actuators, such as, for example, finger-actuated user input buttons each being configured to actuate a different function to be performed by surgical attachment 300. The actuators are in operative mechanical and/or electrical communication with motors 140, 142, 144 such that when a user actuates one of the actuators, a respective one of motors 118, 120, 122 is activated, and in turn actuates a function performed by surgical attachment 300 that is assigned to that particular actuator being actuated.

A first actuator, such as, for example, a first user input button 150 is disposed on a first lateral side 112 of lower hand grip portion 102b and a second actuator, such as, for example, a second user input button 152 is disposed on a second lateral side 114 of lower hand grip portion 102b, opposite first lateral side 112. A third actuator, such as, for example, a third user input button 154 is disposed on a distal side 116 of lower hand grip portion 102b. First user input button 150 is configured to actuate a first function, such as, for example, clamping and unclamping of surgical attachment 300. Second user input button 152 is configured to actuate a second function, such as, for example, rotating of surgical attachment 300. Third user input button 154 is configured to actuate a third function, such as, for example, a closing/opening and/or stapling/cutting function of surgical attachment 300. In some embodiments, user input buttons 150, 152, 154 are assigned to actuate various functions to be carried out by various surgical attachments. It is contemplated that the actuators can be variously configured, such as, for example, as switches, rockers, flaps, latches or levers. In some embodiments, surgical device 100 includes a plurality of actuators situated in various portions of handle housing 102.

When adapter assembly 200 is mated to surgical device 100, in a first connection orientation, each of rotatable drive connectors 118, 120, 122 of surgical device 100 couples with a corresponding drive shaft 218, 220, 222 of adapter assembly 200, as described herein. In this regard, the interface between corresponding first drive connector 118 and first drive shaft 218, the interface between corresponding second drive connector 120 and second drive shaft 220, and the interface between corresponding third drive connector 122 and third drive shaft 222 are keyed such that rotation of each of drive connectors 118, 120, 122 of surgical device 100 causes a corresponding rotation of the corresponding drive shafts 218, 220, 222 of adapter assembly 200.

The mating of drive connectors 118, 120, 122 of surgical device 100 with drive shafts 218, 220, 222 of adapter assembly 200 allows rotational forces to be independently transmitted via each of the three respective connector interfaces. The drive connectors 118, 120, 122 of surgical device 100 are configured to be independently rotated by each respective motor 140, 142, 144 of surgical device 100.

Since each of drive connectors 118, 120, 122 of surgical device 100 has a keyed and/or substantially non-rotatable interface with respective drive shafts 218, 220, 222 of adapter assembly 200, when adapter assembly 200 is coupled to surgical device 100, in a first connection orientation, rotational force(s) are selectively transferred from drive connectors 118, 120, 122 of surgical device 100 to corresponding drive shafts 218, 220, 222 of adapter assembly 200.

The selective rotation of drive connectors 118, 120 and/or 122 of surgical device 100 allows surgical device 100 to selectively actuate different functions of surgical attachment 300. For example, selective and independent rotation of first drive connector 118 of surgical device 100 corresponds to the selective and independent opening and closing of tool assembly 304 of surgical attachment 300, and driving of a stapling/cutting component of tool assembly 304 of surgical attachment 300. As an additional example, the selective and independent rotation of second drive connector 120 of surgical device 100 corresponds to the selective and independent articulation of tool assembly 304 of surgical attachment 300 transverse to longitudinal axis "X-X" (see FIG. 1A). Additionally, for instance, the selective and independent rotation of third drive connector 122 of surgical device 100 corresponds to the selective and independent rotation of surgical attachment 300 about longitudinal axis "X-X" (see FIG. 1A) relative to handle housing 102 of surgical device 100.

Figure 3:
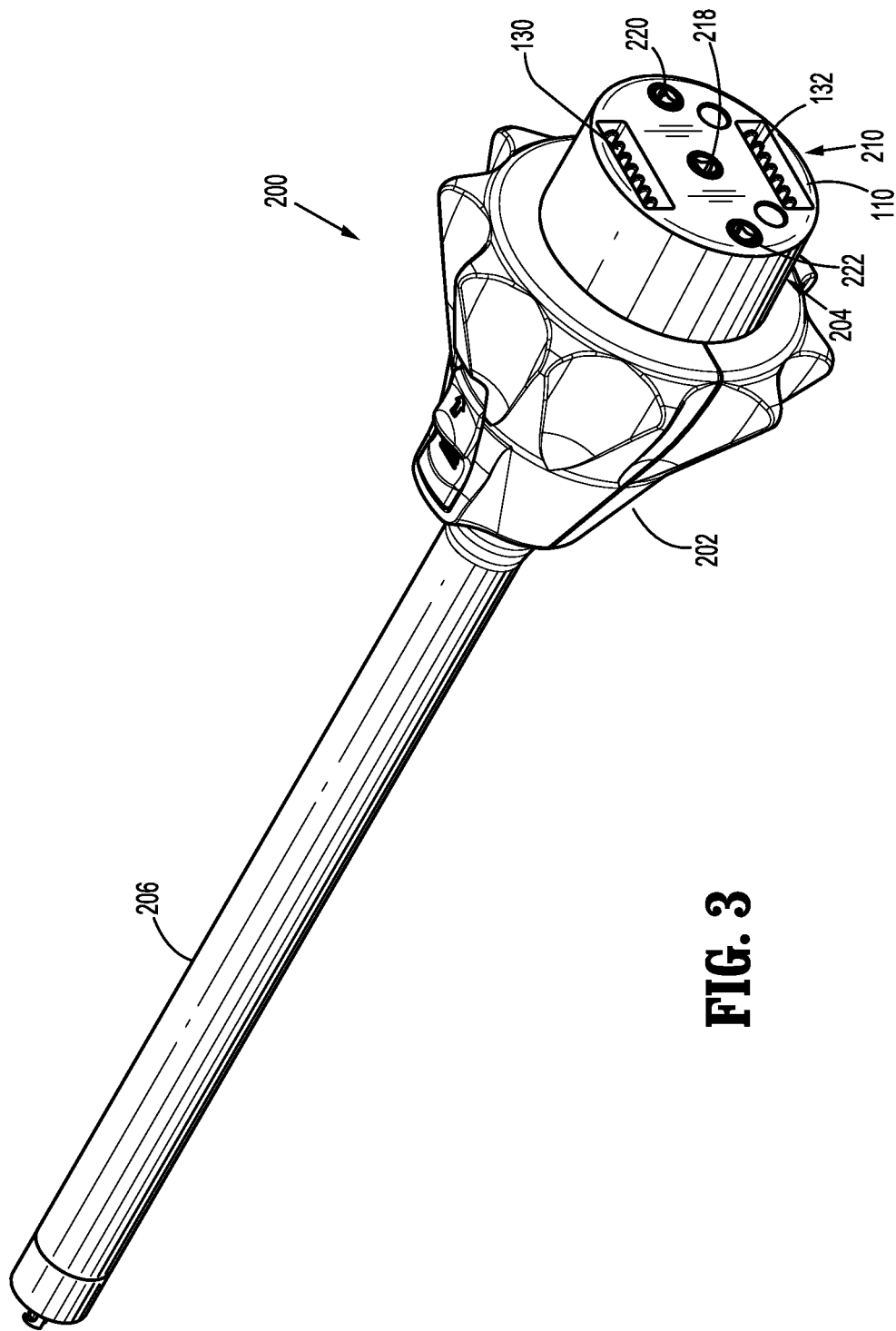
FIG. 3 is a rear, perspective view of the adapter assembly of the system shown in FIGS. 1A, 1B and 2.

Turning to FIGS. 2 and 3, system 10 includes adapter assembly 200 for selectively interconnecting surgical device 100 with surgical attachment 300, as briefly described above. Adapter assembly 200 is in operative communication with motors 140, 142, 144 of surgical device 100 when adapter assembly 200 is coupled to surgical device 100. Adapter assembly 200 functions to transmit rotations of motors 140, 142, 144 to drive the functions to be carried out by surgical attachment 300. Adapter assembly 200 includes an outer knob housing 202 and an outer tube 206 extending from a distal end 242 of knob housing 202. Knob housing 202 and outer tube 206 are configured and dimensioned to house the components of adapter assembly 200. Outer tube 206 is dimensioned for endoscopic insertion. In particular, outer tube 206 is passable through a typical trocar port, cannula or the like. Knob housing 202 is dimensioned to not enter the trocar port, cannula or the like. Knob housing 202 is configured and adapted to connect to a distal end of handle housing 102 of surgical device 100.

Adapter assembly 200 includes a proximal inner housing assembly 204 disposed within knob housing 202. Inner housing assembly 204 defines a proximal end 204a and a distal end 204b. Proximal end 204a includes a mating part, such as, for example, male mating part 210. Male mating part 210 is detachably connectable with connection portion 108 of surgical device 100 such that surgical device 100 and surgical attachment 300 are connectable via adapter assembly 200.

Male mating part 210 is configured to permit coupling of adapter assembly 200 to surgical device 100 in at least a first connection orientation and a second connection orientation. In one embodiment, distal end 242 of inner housing assembly 204 is detachably connectable with a corresponding mating part (not shown) of surgical attachment 100 in a similar manner as adapter assembly 200 is coupled with surgical device 100. Male mating part 210 projects from proximal end 204a of knob housing 202. Male mating part 210 has a substantially circular configuration shaped and configured to fit in connection portion 108 of surgical device 100 such that male mating part 210 and connection portion 108 are connectable in various connection orientations relative to one another.

For example, male mating part 210 of adapter assembly 200 can connect with connection portion 108 of surgical device 100 in a first radial orientation or a second radial orientation relative to connection portion 108. Surgical device 100 and adapter assembly 200 are relatively rotated approximately 180 degrees about longitudinal axis "X-X" to be positioned in either the first or second radial orientations. In some embodiments, male mating part 210 is variously shaped, such as, for example, triangular, oval, square, rectangular, diamond or star-shaped.

Male mating part 210 includes a plurality of mating parts, such as, for example, first drive shaft 218, second drive shaft 220, and third drive shaft 222 rotatably supported in inner housing assembly 204. Drive shafts 218, 220, 222 are arranged in a common plane or line "A2-A2" with one another such that drive shafts 218, 220, 222 are aligned in a symmetrical configuration. Additionally, in the embodiment illustrated in FIGS. 2 and 3, it is contemplated that a second and a third drive shaft 220, 222 may be spaced an equal distance from a first drive shaft 218.

Proximal ends of drive shafts 218, 220, 222 each define a recess configured to matingly engage distal projections of rotatable drive connectors 118, 120, 122 of surgical device 100. As shown in the illustrated embodiment, recesses of drive shafts 218, 220, 222 and distal projections of rotatable drive connectors 118, 120, 122 have non-circular configurations. In some embodiments, various configurations of the recesses and the distal projections are contemplated, such as, for example, triangular, square, rectangular, oval, tapered, oblong, star-shaped, kidney-bean shaped, polygonal and/or non-circular. Each drive shaft 218, 220, 222 functions as a rotation receiving member to receive rotational forces from respective rotatable drive connectors 118, 120, 122 of surgical device 100 during actuation of motors 140, 142, 144.

Drive shafts 218, 220, 222 of adapter assembly 200 are connectable with motors 140, 142, 144, respectively, via rotatable drive connectors 118, 120, 122 of surgical device 100. In the first connection orientation, adapter assembly 200 is engaged to surgical device 100 such that first motor 142 is coupled with second drive shaft 220 of adapter assembly 200 and third motor 144 is coupled with third drive shaft 222 of adapter assembly 200. In the second connection orientation, adapter assembly 200 is engaged to surgical device 100 such that second motor 142 is coupled with third drive shaft 222 of adapter assembly 200 and third motor 144 is coupled with second drive shaft 220 of adapter assembly 200. To move from the first connection orientation to the second connection orientation, adapter assembly 200 can be disconnected from surgical device 100 and rotated approximately 180 degrees along the longitudinal axis "X-X" relative to surgical device 100 and then be reconnected to surgical device 100.

In the illustrated embodiment, in either of the first and second connection orientations, first motor 140 is coupled with first drive shaft 218 of adapter assembly 200 as a result of the straight-lined or planar arrangement of drive shafts 218, 220, 222. However, in alternative embodiments in which drive shafts 218, 220, 222 are arranged in an alternative pattern, for example, a circular pattern, second motor 142 would be coupled with a different drive shaft in each connection orientation.

Adapter assembly 200 is configured to be able to establish or determine the connection orientation with surgical device 100. Male mating part 210 includes electrical contact pin sets 230, 232 connectable with either first electrical plug 130 or second electrical plug 132 of surgical device 100 depending on the connection orientation selected. Electrical contact pin sets 230, 232 are each disposed on opposite sides of the plane "A2-A2" intersecting drive shafts 218, 220, 222 of adapter assembly 200. Electrical contact pin sets 230, 232 may be symmetrically spaced about first drive shaft 218 along a plane "B2-B2." Electrical contact pin sets 230, 232 are capable of determining the connection orientation between surgical device 100 and adapter assembly 200 based on which electrical plug 130, 132 each electrical contact pin set 230, 232 is connected to.

For example, if first and second electrical plugs 130, 132 are connected to first and second electrical contact pin sets 230, 232, respectively, adapter assembly 200 may be preprogrammed to determine that this qualifies as a first connection orientation. If first and second electrical plugs 130, 132 are connected to second and first electrical contact pin sets 232, 230, respectively, adapter assembly 200 may be preprogrammed to determine that this qualifies as a second connection orientation.

Each user input button 150, 152, 154 is assigned to actuate a particular function carried out by surgical attachment 300 depending on the connection orientation determined by adapter assembly 200. Thus, adapter assembly 200 may interchange or reverse the functions actuated by user input buttons 150, 152, 154 of surgical device 100 when the connection orientation of surgical device 100 and adapter assembly 200 moves between the first and second connection orientations. Adapter assembly 200 and/or surgical device 100 may include a processor configured to assign the functions to be actuated by a particular user input button 150, 152, 154 upon adapter assembly 200 recognizing or determining the connection orientation of surgical device 100 and adapter assembly 200.

In some embodiments, when an actuator of surgical device 100 is activated by a user, software checks predefined conditions. If conditions are met, the software controls the motors and delivers mechanical drive to the surgical attachment 300, which can then open, close, rotate, articulate or fire depending on the function of the pressed actuator. The software also provides feedback to the user by turning colored lights on or off in a defined manner to indicate the status of surgical device 100, adapter assembly 200 and/or surgical attachment 300.

Figure 4:
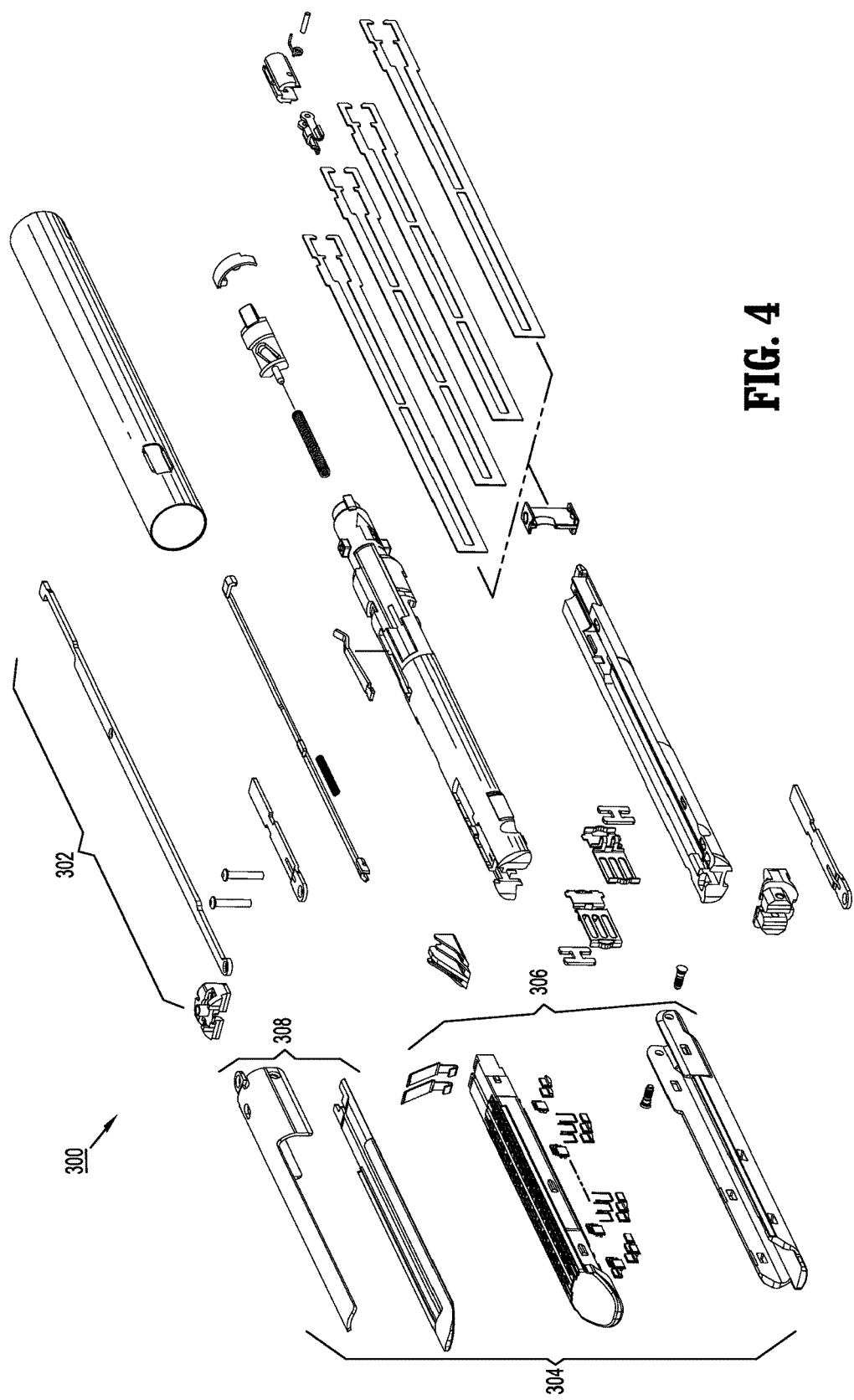
FIG. 4 is a perspective view, with parts separated, of a surgical attachment of the system shown in FIGS. 1A and 1B.

As shown in FIG. 4, system 10 further includes surgical attachment 300. In the illustrated embodiment, surgical attachment 300 extends between a proximal body portion 302 connected to outer body 206 of adapter assembly 200 and a distal tool assembly 304. Proximal body portion 302 may have an arcuate configuration, as shown in FIGS. 1A and 1B. It is contemplated that proximal body portion 302 is variously configured, such as, for example, straight, bent, U-shaped, or V-shaped. Surgical attachment 300 is rotatable relative to outer body 206 about longitudinal axis "X-X." Tool assembly 304 includes a cartridge assembly 306 and an anvil assembly 308. Cartridge assembly 306 includes a stapling and cutting cartridge. Cartridge assembly 306 and anvil assembly 308 are pivotable relative to one another to clamp or unclamp material, such as, for example, tissue, therebetween.

Reference may be made to U.S. Patent Publication No. 2009/0314821, filed on Aug. 31, 2009, entitled "TOOL ASSEMBLY FOR A SURGICAL STAPLING DEVICE" for a detailed discussion of the construction and operation of surgical attachment 300, as illustrated in FIGS. 1A, 1B and 4.

It is contemplated that surgical attachment 300 can be something other than the surgical attachment shown in the illustrated embodiment, such as, for example, a surgical stapler, a surgical cutter, a surgical stapler-cutter, a linear surgical stapler, a linear surgical stapler-cutter, a circular surgical stapler, a circular surgical stapler-cutter, a surgical clip applier, a surgical clip ligator, a surgical clamping device, a vessel expanding device, a lumen expanding device, a scalpel, a fluid delivery device or any other type of surgical instrument. Such surgical instruments are described, for example, in U.S. Pat. Nos. 6,315,184; 6,443,973; 6,264,087; 6,348,061; 6,716,233; 6,533,157; 6,491,201; and 6,488,197; each of which is expressly incorporated herein in its entirety by reference thereto.

In operation, proximal body portion 302 of surgical attachment 300 is engaged to a distal end of outer tube 206 of adapter assembly 200 to connect surgical attachment 300 to adapter assembly 200. In one arrangement, male mating part 210 is inserted within connection portion 108 of surgical device 100, while in the first connection orientation, such that rotatable drive connectors 118, 120, 122 of surgical device 100 engage drive shafts 218, 220, 222 of adapter assembly 200, respectively. First and second electrical contact pin sets 230, 232 of adapter assembly 200 engage first and second electrical plugs 130, 132, respectively, such that outer body 206 of surgical attachment 300 is angled upwards relative to surgical device 100, as shown in FIG. 1A. In so doing, adapter assembly 200 is coupled with surgical device 100 in the first connection orientation.

In another arrangement, male mating part 210 is inserted within connection portion 108 of surgical device 100, while in the second connection orientation, such that rotatable drive connectors 118, 120, 122 of surgical device 100 engage drive shafts 218, 222, 220 of adapter assembly 200, respectively. First and second electrical contact pin sets 230, 232 of adapter assembly 200 engage second and first electrical plugs 132, 130, respectively, such that outer body 206 of surgical attachment 300 is angled downwards relative to surgical device 100, as shown in FIG. 1B. In so doing, adapter assembly 200 is coupled with surgical device 100 in the second connection orientation.

First user input button 150 is configured and adapted to actuate a clamping function of surgical attachment 300 and second user input button 152 is configured and adapted to actuate an unclamping function of surgical attachment 300 when adapter assembly 200 establishes, determines, or recognizes that it is coupled with surgical device 100 in the first connection orientation. In the first connection orientation, when user input button 150 is actuated, tool assembly 304 articulates transverse to longitudinal axis "X-X", and when user input button 152 is actuated, surgical attachment 300 rotates about longitudinal axis "X-X" relative to handle housing 102 of surgical device 100.

A practitioner may prefer that user input buttons 150, 152 be in a reversed orientation on lower hand grip portion 102b of handle housing 102, or a particular surgical procedure may require that surgical device 100 and/or surgical attachment 300 be in an inverted position relative to a practitioner's hand, as shown in FIG. 1B. In such instances, it may preferable that the functions actuated by user input buttons 150, 152 be reversed. System 10 can be preprogrammed or reprogrammed so that the functions assigned to user input buttons 150, 152 in the first connection orientation are to be reversed or interchanged when surgical device 100 is coupled with adapter assembly 200 in the second connection orientation.

In use, adapter assembly 200 is disconnected from surgical device 100 and rotated approximately 180 degrees, about the longitudinal axis "X-X," relative to surgical device 100. Male mating part 210 of adapter assembly 200 is then re-inserted within connection portion 108 of surgical device 100 such that first, second and third rotatable drive connectors 118, 120, 122 of surgical device 100 engage first, third and second drive shafts 218, 222, 220 of adapter assembly, respectively. Further, first and second electrical connector pin sets 230, 232 of adapter assembly 200 engage second and first electrical plugs 132, 130, respectively, such that outer body 206 of surgical attachment 300 is oriented in a different orientation relative to surgical device 100, as shown in FIG. 1B. In so doing, adapter assembly 200 is coupled with surgical device 100, in the second connection orientation. Once adapter assembly 200 is re-coupled with surgical device 100, surgical device 100 determines, establishes or recognizes that the adapter assembly 200 is coupled thereto in the second connection orientation.

In the second connection orientation, when user input button 150 is actuated, surgical attachment 300 rotates about longitudinal axis "X-X" relative to handle housing 102 of surgical device 100, and when user input button 152 is actuated, tool assembly 304 articulates transverse to longitudinal axis "X-X", thus reversing the functions actuated by user input buttons 150, 152.

In one embodiment, adapter assembly 200 is configured to provide surgical device 100 with the capability to actuate surgical attachment 300 in a plurality of speed settings depending on the requirements of a particular application. Adapter assembly 200 is connectable with surgical device 100 in a plurality of connection orientations, as described herein. Each orientation of the plurality of orientations corresponds to a different rate of motion of surgical attachment 300 when surgical attachment 300 is actuated. In use, if a practitioner desires to adjust the actuation speed of surgical attachment 300, the connection orientation between adapter assembly 200 and surgical device 100 is changed, in a similar manner described above, such that the adapter assembly 200 changes the speed of actuation of surgical attachment to a speed corresponding to the connection orientation selected.

Any of the components described herein may be fabricated from either metals, plastics, resins, composites or the like taking into consideration strength, durability, wearability, weight, resistance to corrosion, ease of manufacturing, cost of manufacturing, and the like.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

What is claimed is:

1. An electromechanical surgical system, comprising:
a hand-held electromechanical surgical device configured to actuate a surgical attachment, the surgical device including:
a housing;
first and second actuators each being configured to actuate a different function of the surgical attachment; and
at least one motor disposed with the housing for driving actuation of the surgical attachment; and
an adapter assembly for selectively interconnecting the surgical device with the surgical attachment, the adapter assembly being in operative communication with the at least one motor and including at least one mating part adapted to be detachably connected to the surgical device and configured to permit coupling of the adapter assembly to the surgical device in at least a first connection orientation and a second connection orientation, wherein in the first connection orientation the first actuator is configured to actuate a first function of the surgical attachment and the second actuator is configured to actuate a second function of the surgical attachment, and in the second connection orientation the first actuator is configured to actuate the second function of the surgical attachment and the second actuator is configured to actuate the first function of the surgical attachment.

2. An electromechanical surgical system as recited in claim 1, wherein the first and second actuators include user input buttons.

3. An electromechanical surgical system as recited in claim 1, wherein the at least one motor includes a first motor adapted to be connected with a first drive shaft of the adapter assembly for performing the first function of the surgical attachment and a second motor adapted to be connected with a second drive shaft of the adapter assembly for performing the second function of the surgical attachment.

4. An electromechanical surgical system as recited in claim 3, wherein in the first connection orientation the first motor is coupled with the first drive shaft and the second motor is coupled with the second drive shaft, and in the second connection orientation the first motor is coupled with the second drive shaft and the second motor is coupled with the first drive shaft.

5. An electromechanical surgical system as recited in claim 1, wherein the adapter assembly is configured to interchange functions actuated by the surgical device when the adapter assembly moves between the first connection orientation and the second connection orientation.

6. An electromechanical surgical system as recited in claim 1, wherein the at least one mating part includes an electrical connector adapted for connection with an electrical connector of the surgical device.

7. An electromechanical surgical system, comprising:
a hand-held electromechanical surgical device configured to actuate a surgical attachment, the surgical device including:
a housing;
a first motor disposed with the housing; and
a second motor disposed with the housing; and
an adapter assembly for selectively interconnecting the surgical device with the surgical attachment, the adapter assembly including:
at least one mating part adapted to be detachably connected to the surgical device and configured to permit coupling of the adapter assembly to the surgical device in at least a first connection orientation and a second connection orientation;
a first drive shaft configured to actuate a first function of the surgical attachment; and
a second drive shaft configured to actuate a second function of the surgical attachment, wherein in the first connection orientation the first motor is coupled with the first drive shaft and the second motor is coupled with the second drive shaft, and in the second connection orientation the first motor is coupled with the second drive shaft and the second motor is coupled with the first drive shaft.

\* \* \* \* \*